United States Patent
Catinat (10) Patent No.: US 9,159,937 B2
(45) Date of Patent: Oct. 13, 2015

(54) HETEROLEPTIC LIGHT-EMITTING COMPLEXES

(71) Applicant: SOLVAY SA, Brussels (BE)

(72) Inventor: Jean-Pierre Catinat, Waudrez (BE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 14/369,450

(22) PCT Filed: Dec. 20, 2012

(86) PCT No.: PCT/EP2012/076329
§ 371 (c)(1),
(2) Date: Jun. 27, 2014

(87) PCT Pub. No.: WO2013/098177
PCT Pub. Date: Jul. 4, 2013

(65) Prior Publication Data
US 2015/0011764 A1   Jan. 8, 2015

(30) Foreign Application Priority Data

Dec. 28, 2011  (EP) .................................... 11010252
Jun. 15, 2012  (EP) .................................... 12004540

(51) Int. Cl.
| | | |
|---|---|---|
| *C07F 15/00* | (2006.01) |
| *H01L 51/50* | (2006.01) |
| *H01L 51/00* | (2006.01) |
| *C09K 11/06* | (2006.01) |
| *H05B 33/14* | (2006.01) |
| *H05B 33/18* | (2006.01) |
| *C07F 5/06* | (2006.01) |

(52) U.S. Cl.
CPC ............ *H01L 51/0085* (2013.01); *C07F 5/069* (2013.01); *C07F 15/0033* (2013.01); *C09K 11/06* (2013.01); *H01L 51/5012* (2013.01); *H01L 51/5016* (2013.01); *H05B 33/14* (2013.01); *H05B 33/18* (2013.01); *C09K 2211/1029* (2013.01); *C09K 2211/1044* (2013.01); *C09K 2211/185* (2013.01); *C09K 2211/188* (2013.01)

(58) Field of Classification Search
USPC .............................................. 546/10; 313/504
See application file for complete search history.

(56) References Cited

U.S. PATENT DOCUMENTS

| | | | |
|---|---|---|---|
| 8,795,850 B2* | 8/2014 | Kottas et al. ................... | 428/690 |
| 2006/0078758 A1 | 4/2006 | Lin | |
| 2006/0251923 A1 | 11/2006 | Lin et al. | |
| 2011/0057559 A1* | 3/2011 | Xia et al. ....................... | 313/504 |

FOREIGN PATENT DOCUMENTS

| | | |
|---|---|---|
| EP | 2 062 959 A2 | 5/2009 |
| EP | 2 066 150 A1 | 6/2009 |
| JP | 2007 123392 A | 5/2007 |
| JP | 2009 096861 A | 5/2009 |
| WO | 2011/024733 A1 | 3/2011 |
| WO | 2011/070987 A1 | 6/2011 |

OTHER PUBLICATIONS

Zhe Liu et al: "Organometallic Iridium(III) Cyclopentadienyl Anticancer Complexes Containing C,N-Chelating Ligands", Organometallics, vol. 30, No. 17, Aug. 5, 2011, pp. 4702-4710.

* cited by examiner

*Primary Examiner* — Charanjit Aulakh (57) ABSTRACT

Heteroleptic light emitting complexes having the general formula $M(L_1)_n(L_2)_m$, wherein a) $L_1$ has the formula E1-E2, wherein E1 is a 6-membered heteroaryl ring bound to the metal atom M by a dative bond and containing at least one donor hetero atom and E2 is bound to the metal atom by covalent or dative bonds and is selected from the group consisting of substituted or unsubstituted $C_5$-$C_{30}$ aryl and substituted or un-substituted $C_2$-$C_{30}$ heteroaryl groups, b) ligand $L_2$ is selected from the group consisting of 1-(2,6 disubstituted phenyl)-2-phenyl-1 H-imidazole ligands or 5-(2,6 disubstituted phenyl)-1-phenyl-1 H-pyrazole ligands, and c) M is a non-radioactive transition metal with an atomic number of at least 40 and the sum of m and n is equal to half of the bond valency of metal M.

12 Claims, 1 Drawing Sheet

Fig.1: Room T° emission spectra in 2-MetTHF solutions (Fluoromax)

Fig. 2: Room T° emission spectra in 2-MetTHF solutions (Hamamatsu)

HETEROLEPTIC LIGHT-EMITTING COMPLEXES

This application is a U.S. national phase entry under 35 U.S.C. §371 of International Application No. PCT/EP2012/076329, filed on Dec. 20, 2012, which claims priority to European Application No. 11010252.2, filed on Dec. 28, 2011, and European Application No. 12004540.6, filed Jun. 15, 2012, the entirety of all of which is being incorporated herein by reference for all purposes.

The present invention relates to novel tris heteroleptic phosphorescent iridium complexes.

Today, various light-emitting devices are under active study and development, in particular those based on electroluminescence (EL) from organic materials.

In the contrast to photoluminescence, i.e. the light emission from an active material as a consequence of optical absorption and relaxation by radiative decay of an excited state, electroluminescence (EL) is a non-thermal generation of light resulting from the application of an electric field to a substrate. In this latter case, excitation is accomplished by recombination of charge carriers of contrary signs (electrons and holes) injected into an organic semiconductor in the presence of an external circuit.

A simple prototype of an organic light-emitting diode (OLED), i.e. a single layer OLED, is typically composed of a thin film of an active organic material which is sandwiched between two electrodes, one of which needs to have a degree of transparency sufficient in order to observe light emission from the organic layer.

If an external voltage is applied to the two electrodes, charge carriers, i.e. holes, at the anode and electrons at the cathode are injected to the organic layer beyond a specific threshold voltage depending on the organic material applied. In the presence of an electric field, charge carriers move through the active layer and are non-radiatively discharged when they reach the oppositely charged electrode. However, if a hole and an electron encounter one another while drifting through the organic layer, excited singlet and triplet states, so-called excitons, are formed. Light is thus generated in the organic material from the decay of molecular excited states (or excitons). For every three triplet excitons that are formed by electrical excitation in an OLED, one state with antiparallel spins (singlet) exciton is created.

Many organic materials exhibit fluorescence (i.e. luminescence from a spin-allowed process) from singlet excitons: since this process occurs between states of same spin multiplicity it may be very efficient. On the contrary, if the spin multiplicity of an exciton is different from that of the ground state, then the radiative relaxation of the exciton is spin-forbidden and luminescence will be slow and inefficient. Because the ground state is usually a singlet, decay from a triplet breaks spin symmetry: the process is thus forbidden and efficiency of EL is very low. Thus the energy contained in the triplet states is mostly wasted.

Phosphorescence emission is a phenomenon of light emission in the relaxation process between two states of different spin multiplicity, often between a triplet and a singlet, but because the relaxation process is normally conducted by thermal deactivation, it is in many cases not possible to observe phosphorescence emission at room temperature. Characteristically, phosphorescence may persist for up to several seconds after excitation due to the low probability of the transition, in contrast to fluorescence which originates in the rapid decay.

The theoretical maximum internal quantum efficiency of light-emitting devices comprising light-emitting materials based on an emission phenomenon in the relaxation process from a singlet excited state (i.e. fluorescence emission), is at maximum 25% because in organic EL devices, the ratio of the singlet to the triplet state in the excited state of light-emitting materials is always 25:75. By using phosphorescence emission (emission from triplet states) this efficiency could be raised to the theoretical limit of 100%, thereby significantly increasing the efficiency of the EL device.

Thus, successful utilization of phosphorescent materials holds enormous promises for organic electroluminescent devices. As mentioned above, it is difficult to get phosphorescence emission from an organic compound because of low probability of intersystem crossing and concurrent thermal deactivation of the triplet relaxation process. However, it has been found that the presence of heavy atoms favours spin orbit coupling and therefore intersystem crossing is enhanced. This is also true when "organic" ligands are coordinated to heavy metal, showing phosphorescence because of the spin-orbit interaction resulting from the heavy metal atom effect. Accordingly, a number of phosphorescent materials having iridium or platinum as a heavy metal have been developed.

For the manufacture of OLED's it is advantageous to deposit the emitting layer (which usually comprises a host and a phosphorescent dopant) via a solution based process, which requires, however, emitters having a sufficient solubility in the suitable solvents. The concentration of the phosphorescent dopant has to be high enough to efficiently harvest the triplet excitons generated on the host in the emitting layer. If the solubility of the phosphorescent dopant is too low, it is difficult if not impossible to achieve the optimum doping levels required via a process in solution.

The most commonly used phosphorescent emitters in EL devices are Ir and Pt complexes. However, these complexes show normally a very low solubility and thus have to be incorporated into the EL devices by vacuum deposition, which is time and cost consuming.

Attempts have been made to improve the solubility of homoleptic phosphorescent complexes by adding solubilizing substituents on the ligands but the results achieved are not fully satisfactory and the additional substituents tend to lower the glass transition temperature in certain cases which can lead to problems during operation of the OLED devices.

N-(2,6-disubstituted phenyl) 2-phenyl imidazole ligands have been described as ligands in homoleptic and heteroleptic phosphorescent transition metal complexes. N-(2,6-dimethylphenyl) 2-phenyl imidazole is commonly referred to as mc3-ligand and N-(2,6-diisopropylphenyl) 2-phenyl imidazole is commonly referred to as mc6-ligand.

Heteroleptic complexes comprising mc3 or mc6-type ligands are e.g. disclosed in US 2007/088187, which describes general formulae mc12 and mc11 (as designated in this reference):

mc11

-continued mc12 wherein each R can be the same or different and can be hydrogen, hydrocarbyl and heteroatom substituted hydrocarbyl, cyano and F and two of R may be linked to form a ring, m is 1, 2 or 3 and n is an integer satisfying the valency of M and M is a transition metal. No examples for compounds of mc12-type structures are given.

US2011/057559 discloses heteroleptic complexes of mc3 and mc6 type ligands bearing an aryl or a substituted aryl group in at least one of positions 3 to 5 of the ring bearing the methyl or isopropyl groups.

WO2010/056669 discloses a compound with a 2-phenyl pyridine ligand and a mc6 type ligand where the imidazole ring is annealed with a phenyl ring.

WO2010/129323 shows a complex (compound 57) with two 2-phenyl pyridine ligands and one mc6 ligand, where the imidazole ring is annealed with a phenyl ring and where the hydrogen atoms of the isopropyl groups are replaced by deuterium atoms.

US 2009/0243479 describes electroluminescent elements comprising compounds having the partial structure wherein $R^1$ is a substituent having 4 to 20 carbon atoms and $R^2$ to $R^4$ represent a substituent, Q is a group of atoms necessary to form an aromatic hydrocarbon ring or an aromatic heterocyclic ring and $n_2$, $n_3$ and n4 are 0 or an integer. Preferably Q is a phenyl ring. The compounds of the above structure can be used in homoleptic and heteroleptic complexes. The disclosed heteroleptic complexes involve two different types of 2-phenylimidazole ligand.

JP-A 2009/096861 discloses electroluminescent elements containing homoleptic or heteroleptic metal complexes comprising a 1-phenylpyrazole ligand. In case of heteroleptic complexes, the second ligand comprises a phenyl ring and a 5-membered heteroaryl ring.

Most of the OLED devices for both display and lighting applications based on organometallic complexes are prepared through vacuum deposition which is inherently limited in terms of cost, substrate size and volume. To fully realize their potential as mass market application, OLEDs need to be fabricated by low cost, large area manufacturing processes such as roll-to-roll printing processes, requiring the development of soluble materials that can be printed. In this context new phosphorescent emitters with enhanced solubility and dispersion properties need to be developed as the majority of phosphorescent emitters are not soluble enough in organic solvent.

Phosphorescent organometallic dendrimers have been proposed to circumvent these problems. Dendritic structures may facilitate solution processability and prevent concentration dependent self-quenching of the complexes. For example, WO2002/066552 discloses dendrimers having metal ions as part of the core. The metal chromophore at the core of the dendrimer will be relatively isolated from core chromophores of adjacent molecules, which is proposed to minimize concentration quenching. Other non-dendritic bulky ligands could have the same effect on device performance.

The tris homoleptic complex fac-Ir(2-PhQ)$_3$ complex involving a 2-phenylquinoline ligand (=2-PhQ) is a well-known orange emitter which could lead to high lifetime in vapor-processed devices. But its solubility in most organic solvents is too low to be processed by solution. (e.g. <0.02 wt % in toluene).

The introduction of solubilizing groups in position 4 (in para position to the quinoline moiety) of the phenyl ring of the phenylquinoline ligand can be successfully used to increase the solubility of the complexes. Thus, introduction of an n-hexyl group in position 4 increases the solubility to more than 1 wt % in toluene. However, addition of such groups leads to a decrease in glass transition temperature which is undesirable as it leads to a thermal instability of the films obtained, limiting its uses in organic electronic devices.

Introduction of t-butyl or cyclohexyl groups into tris homoleptic complexes while not being as detrimental to glass transition temperature as n-hexyl, have only a limited positive effect on the solubility of the homoleptic complexes.

It was an object of the present invention to provide light emitting materials with an improved solubility without detrimentally influencing other properties like e.g. glass transition temperature and emission properties (photoluminescence quantum yield, emission color).

This object is achieved with the light emitting heteroleptic complexes in accordance with claim 1.

Preferred embodiments of the light emitting complexes in accordance with the present invention are set forth in the dependent claims and the detailed description and the examples hereinafter.

Surprisingly it has been found that heteroleptic complexes having the general formula $M(L_1)_n(L_2)_m$ wherein a) $L_1$ is a bidentate ligand and has the formula E1-E2, wherein

E1 is a 6-membered heteroaryl ring bound to the metal atom M by a dative bond and containing at least one donor hetero atom, wherein said heteroaryl ring may be un-substituted or substituted by substituents selected from the group consisting of halogen, alkyl, alkoxy, amino, cyano, alkenyl, alkynyl, arylalkyl, aryl and heteroaryl group and/or may form an annealed ring system with other rings selected from cycloalkyl, aryl and heteroaryl rings, and E2 is bound to the metal atom M by covalent or dative bonds and is selected from the group consisting of substituted or un-substituted $C_5$-$C_{30}$ aryl and substituted or un-substituted $C_2$-$C_{30}$ heteroaryl groups, which E2 group may be un-substituted or substituted by substituents selected from the group consisting of halogen, alkyl, alkoxy, amino, cyano, alkenyl, alkynyl, arylalkyl, aryl and heteroaryl groups and E1 and E2 are linked via a covalent bond, b) ligand $L_2$ is selected from the group consisting of 1-(2,6 disubstituted phenyl)-2-phenyl-1H-imidazole ligands or 5-(2,6 disubstituted phenyl)-1-phenyl-1H-pyrazole ligands of formulae 1 or 2 wherein $R^1$ and $R^2$, which may be the same or different, represent a group other than H like a $C_1$ to $C_{20}$ alkyl or haloalkyl group, a cycloalkyl group, a $C_5$ to $C_{30}$ aryl group or a $C_2$ to $C_{30}$ heteroaryl group, said cycloalkyl, aryl and heteroaryl groups being un-substituted or substituted by substituents selected from the group consisting of halogen, alkyl, alkoxy, amino, cyano, alkenyl, alkynyl, arylalkyl, aryl and heteroaryl groups and $R^3$ is selected from the group consisting of H, halogen, $NO_2$, CN, $N(R^4)_2$, $B(OR^4)_2$, COOH, $C(O)R^4$, $CO_2R^4$, CON$(R^4)_2$, $OR^4$, $SR^4$, $SO_3H$, $S(\!=\!O)R^4$, $S(\!=\!O)_2R^4$, $P(R^4)_2$, $P(\!=\!O)(R^4)_2$, $Si(R^4)_3$, alkyl, cycloalkyl, haloalkyl, alkoxy, alkenyl, alkynyl, aryl, alkylaryl, heteroaryl, substituted heteroaryl and heterocyclic groups, with the proviso that $R^3$ is not aryl if ligand $L_2$ is represented by formula (1), $R^4$ which may be the same or different, are selected from the group consisting of H, alkyl, alkenyl, alkynyl, aryl, substituted aryl, alkylaryl, halogen, heteroaryl, substituted heteroaryl and heterocyclic groups, R and R', independently of one another, are selected from the group consisting of H, halogen, $NO_2$, CN, $N(R^5)_2$, $B(OR^5)_2$, COOH, $C(O)R^5$, $CO_2R^5$, $CON(R^5)_2$, $OR^5$, $SR^5$, $SO_3H$, $S(\!=\!O)R^5$, $S(\!=\!O)_2R^5$, $P(R^5)_2$, $P(\!=\!O)(R^5)_2$, $Si(R^5)_3$, alkyl, alkenyl, alkynyl, aryl, substituted aryl, alkylaryl, heteroaryl, substituted heteroaryl and heterocyclic groups, $R^5$ which may be the same or different, are selected from the group consisting of H, alkyl, alkenyl, alkynyl, aryl, substituted aryl, alkylaryl, halogen, heteroaryl, substituted heteroaryl and heterocyclic groups, a is an integer of from 0 to 3 and b is an integer of from 0 to 2, and c is an integer of from 0 to 3, preferably of from 0 to 1.

c) M is a non-radioactive transition metal with an atomic number of at least 40, preferably selected from the group consisting of Ir, Os, Rh, Ru or Pt, most preferably Ir and the sum of m and n is equal to half of the bond valency of metal M, provide a good balance of solubility, glass transition temperature and emission properties.

E1 is preferably bound to the metal atom M through a donor heteroatom, more preferably through a neutral nitrogen donor atom.

Thus, E1 in ligand $L_1$ is preferably selected from the following 6-membered heteroaryl rings which may be un-substituted or substituted by substituents selected from the group consisting of halogen, alkyl, alkoxy, amino, cyano, alkenyl, alkynyl, arylalkyl, aryl and heteroaryl groups and/or may form an annealed ring system with other rings selected from cycloalkyl, aryl and heteroaryl rings.

E2 in ligand $L_1$ is preferably selected from unsubstituted or substituted aryl groups, heteroaryl groups as defined above for E1, un-substituted or substituted carbazolyl groups, un-substituted or substituted dibenzofuranyl groups or from the following heteroaryl groups -continued which may be un-substituted or substituted by substituents (e.g. substituent R") selected from the group consisting of halogen, alkyl, alkoxy, amino, cyano, alkenyl, alkynyl, arylalkyl, aryl and heteroaryl groups and/or may form an annealed ring system with other rings selected from cycloalkyl, aryl and heteroaryl rings.

Particularly preferably E2 is an aryl group selected from the group consisting of phenyl, biphenyl, napththyl or anthracenyl. Particularly preferred heteroaryl group E2 is un-substituted or substituted carbazolyl or un-substituted or substituted dibenzofuranyl. Especially preferably E2 is phenyl.

Subunits E1 and E2 of ligand $L_1$ are linked through a covalent bond.

$R^3$ in formulae (1) and (2) is preferably selected from hydrogen or $C_1$ to $C_{20}$ alkyl and substituent $R^3$ is preferably attached in meta position to substituents $R^1$ and $R^2$.

$R^1$ and $R^2$ are preferably selected from $C_1$ to $C_{20}$ alkyl or $C_5$ to $C_{30}$ aryl groups, $C_1$ to $C_{20}$ alkyl groups being particularly preferred. In accordance with a particularly preferred embodiment $R^1$ and $R^2$, independent of one another are selected from $C_1$ to $C_8$ alkyl and especially preferred at least one of $R^1$ and $R^2$ is methyl or isopropyl. Particularly preferred complexes comprise identical substituents $R^1$ and $R^2$.

According to a further preferred embodiment, ligand $L_2$ is selected from 1-(2,6 disubstituted phenyl)-2-phenyl-1H-imidazole ligands of formula (1)

(1)

wherein R, R', $R^1$, $R^2$, a, b and c are as defined in claim 1 and $R^3$ is H or a $C_1$ to $C_{20}$ alkyl group. According to a first preferred embodiment a and b are zero, i.e. no substituents R and R' are present. According to another preferred embodiment at least one of substituents R and R' is present. The introduction of substituents R and R' has shown a further increase in solubility in certain cases.

According to a still further preferred embodiment, ligand $L_2$ is selected from 5-(2,6 disubstituted phenyl)-1-phenyl-1H-pyrazole ligands of formula (2),

(2)

wherein R, R', $R^1$, $R^2$, a, b and c are as defined in claim 1 and $R^3$ is H or a $C_1$ to $C_{20}$ alkyl group. According to a first preferred embodiment a and b are zero, i.e. no substituents R and R' are present. According to another preferred embodiment at least one of substituents R and R' is present. The introduction of substituents R and R' has shown a further increase in solubility in certain cases.

An especially preferred embodiment in accordance with the present invention is represented by heteroleptic complexes with ligands of formula (2) as ligands $L_2$ and 2-phenylpyridine ligands as ligands $L_1$.

In accordance with another preferred embodiment the triplet energy level of ligand $L_2$ is higher than the triplet energy level of ligand $L_1$ and accordingly complexes with a respective combination of ligands constitute another preferred embodiment of the present invention. If the triplet energy level of ligand $L_2$ is higher than the triplet energy level of ligand $L_1$ it is reasonable to expect that the emission will remain in the same range of color as the homoleptic $[Ir(L_1)_3]$ complexes. By selecting such a ligand $L_2$ it should thus be possible to keep the emission of the heteroleptic complexes in the same range as the homoleptic complexes involving the sole ligand $L_1$ while improving the solubility.

In accordance with still another preferred embodiment of the present invention, $L_1$ is selected from substituted or unsubstituted 2-phenylquinoline and substituted or unsubstituted 1-phenylisoquinoline ligands of formulae (3) and (4)

(3)

-continued (4)

wherein $R^8$ to $R^{13}$, which may be the same or different at each occurrence, are selected from the group consisting of H, halogen, $NO_2$, CN, $N(R^6)_2$, $B(OR^6)_2$, COOH, $C(O)R^6$, $CO2R^6$, $CON(R^6)_2$, $OR^6$, $SR^6$, $SO_3H$, $S(=O)R^6$, $S(=O)_2R^6$, $P(R^6)_2$, $P(=O)(R^6)_2$, $Si(R^6)_3$, alkyl, alkenyl, alkynyl, aryl, substituted aryl, alkylaryl, heteroaryl, substituted heteroaryl and heterocyclic groups, with $R^6$, which may be the same or different, being selected from the group consisting of H, alkyl, alkenyl, alkynyl, aryl, substituted aryl, alkylaryl, halogen, heteroaryl, substituted heteroaryl and heterocyclic groups, p, u and v, independent of one another, represent an integer of from 0 to 4, t represents an integer of from 0 to 3 and s and w, independent of one another represent an integer of from 0 to 2. In accordance with especially preferred embodiments at least one of p, s, t, u, v and w is zero. In certain cases the introduction of substituents in the respective rings has yielded a further improvement in solubility.

In accordance with a further preferred embodiment of the present invention, the heteroleptic light emitting complexes are represented by the formulae (5) to (8):

(5)

(6)

(7)

(8)

wherein $R^1$ to $R^3$ are as defined in claim 1. Preferably $R^1$ and $R^2$ are the same and methyl or isopropyl. R3 is preferably hydrogen or an alkyl group.

The phenylquinoline and phenylisoquinoline type ligands in formulae (5) to (8) may carry one or more substituents as defined above for formulae (3) and (4).

The light emitting materials in accordance with the present invention may be prepared using known methods described in the literature for respective compounds, so that detailed explanations are not necessary here. A preferred process to prepare heteroleptic complexes in accordance with the present invention combining ligands of formula 1 or 2 with ligands of formula 3 or 4 comprises reacting a halo-bridged dimer of general formula $[(L_1)_nM(\mu-X)2M(L_1)_n]$ with a ligand compound of formula $L_2$-H or a halo-bridged dimer of general formula $[(L_2)_nM(\mu-X)2-M(L_2)_n]$ with a ligand compound of formula $L_1$-H where ($\mu$-X) represents a bridging halide, in a solvent mixture of an organic solvent and water comprising more than 25 vol % of water at a temperature of from 50 to 260° C., optionally in the presence of from 0 to 5 molar equivalents, relative to the number of moles of halide $X^-$ ion introduced into the reaction mixture through the halo-bridged dimer, of a scavenger for halide $X^-$ ion and of from 0 to less than 1 molar equivalent, based on the molar amount of transition metal in the halo-bridged dimer, of an added salt and of from 0 to 10 vol %, based on the total volume of the solvent mixture, of a solubilisation agent increasing the solubility of the halo-bridged dimer in the reaction mixture.

Generally, the heteroleptic complexes in accordance with the present invention can be obtained in yields superior or at least equal to 30% by using this process. The heteroleptic complexes $Ir(L_1)_n(L_2)_m$ in accordance with the present invention have been prepared following this process by reacting a halo-bridged dimer of general formula $[(L_1)_2Ir(\mu-Cl)_2-Ir(L_1)_2]$ with a ligand compound of formula $L_2$-H or a halo-bridged dimer of general formula $[(L_2)_2Ir(\mu-Cl)_2-Ir(L_2)_2]$ with a ligand compound of formula $L_1$-H where ($\mu$-Cl) represents a bridging chloride in a solvent mixture of an organic solvent and water comprising more than 25 vol % of water at a temperature of from 50 to 260° C., optionally in the presence of from 0 to 5 molar equivalents, relative to the number of moles of halide $X^-$ ion introduced into the reaction mixture through the halo-bridged dimer, of a scavenger for halide $X^-$ ion. In accordance with this process, the reaction of halo bridged dimer with ligand compound is carried out in a mixture of an organic solvent and water, which mixture comprises more than 25 vol % of water. The mixture preferably contains not more than 70 vol. % of an organic solvent and at least 30 vol. % of water, and more preferably not more than 66 vol. % of an organic solvent and at least 34 vol. % of water. A water content of 40 to 60% by volume has proven to be particularly suitable.

The organic solvent may be any solvent which is miscible with water to form a single phase, i.e. a solution. Preferably, the organic solvent may be at least one selected from a group consisting of $C_1$–$C_{20}$ alcohols, for example, methanol, ethanol, n-propanol, isopropanol, n-butanol, isobutanol or tert-butanol, oxane, for example, dioxane or trioxane, $C_1$–$C_{20}$ alkoxyalkyl ethers, for example, bis(2-methoxyethyl) ether, $C_1$-$C_{20}$ dialkyl ethers, for example, dimethyl ether, $C_1$–$C_{20}$ alkoxy alcohols, for example, methoxyethanol or ethoxyethanol, diols or polyalcohols, for example, ethylene glycol, propylene glycol, triethylene glycol or glycerol, polyethylene glycol, or dimethyl sulfoxide (DMSO), N-methyl pyrrolidone (NMP) or dimethyl formamide (DMF), and combinations thereof. More preferably, the organic solvent may be at least one selected from a group consisting of dioxane, trioxane, bis(2-methoxyethyl) ether, 2-ethoxyethanol and combinations thereof. Most preferably, the organic solvent is dioxane or bis(2-methoxyethyl) ether (hereinafter referred to as diglyme)

The reaction temperature is in the range of from 50 to 260° C., preferably in the range of from 80 to 150° C. In some specific embodiments, the isomer is prepared at a pressure of from $1\times10^3$ to $1\times10^8$ Pa, preferably $1\times10^4$ to $1\times10^7$ Pa, and most preferably $1\times10^5$ to $1\times10^6$ Pa.

The ligand compound L-H is preferably used in a molar excess, relative to the amount of metal in the halo-bridged dimer. In a more specific embodiment, the ligand compound is used in an amount of 10 to 3000 mol percent excess, preferably 50 to 1000 mol percent excess, most preferably 100 to 800 mol percent excess.

This process can be carried out in the presence or in the absence of a scavenger for halide ion $X^-$. If halide ion scavenger is present, it is used in amount of up to 5, preferably up to 3 moles per mole of halide $X^-$ ion introduced into the reaction mixture through the halo-bridged dimer. Preferred scavengers are silver salts. Most preferred silver salts are tetrafluoroborate, trifluoroacetate or triflate.

The process can be carried out in the absence of any added salts. In certain cases, where the solubility of the halo-bridged dimer in the solvent mixture is very low, it has proven to be advantageous to add up to 10 vol %, preferably of from 0.1 to 10 vol %, even more preferably of from 0.5 to 5 vol %, based on the volume of the solvent mixture, of a solubilising agent to improve the solubility of the dimer in the reaction solvent. DMSO has shown to work particularly well as solubilizing agent in certain cases.

The light-emitting heteroleptic complexes $[M(L_1)_n(L_2)_m]$ in accordance with the present invention, which combine bidentate $L_1$ ligands having the formula E1-E2 as defined in claim 1 and bidentate $L_2$ ligands selected from formulae 1 or 2, have a number of advantageous properties as compared to homoleptic complexes $[M(L_1)_{m+n}]$ involving the sole $L_1$ ligand and to more "classical" heteroleptic complexes $[M(L_1)_n(acac)_m]$ and $[M(L_1)_n(pic)_m]$ involving the $L_1$ ligand as "main" ligand and acetylacetonate (=acac) or picolinate (=pic) or their derivatives as "ancillary" ligand.

The heteroleptic complexes in accordance with the present invention show largely increased solubilities in organic solvents as compared to their counterpart homoleptic complexes: an increase by a factor of at least 10 could be achieved. This is a highly important advantage in the course of the manufacture of organic electronic devices by solution processing and thus constitutes a significant economic and technical advantage. Attempts have been made to improve the solubility of homoleptic complexes by addition of solubilizing substituents on the ligands but the results achieved are not fully satisfactory. Solubility could indeed be improved but it could be at the expense of the glass transition temperature $T_g$ which concomitantly could become very low, e.g. when using a n-hexyl group as solubilizing substituents, leading to problems during operation of the OLED devices. On the contrary, the heteroleptic complexes in accordance with the present invention allow to combine large solubilities with high Tg values.

Provided that the triplet energy level of $L_2$ ligand is higher than the triplet energy level of $L_1$ ligand, which is e.g. the case when $L_2$ ligand is selected from formulae 1 or 2 while $L_1$ ligand is selected from formulae 3 or 4, the emission of the heteroleptic complexes $[M(L_1)_n(L_2)_m]$ in accordance with the present invention could be kept in the same color range as their counterpart homoleptic complexes $[M(L_1)_{m+n}]$. Moreover, the heteroleptic complexes $[M(L_1)_n(L_2)_m]$ in accordance with the present invention emit almost as efficiently as their counterpart homoleptic complexes leading to about the same photoluminescence quantum yield values. So by properly selecting the $L_2$ ligand, the heteroleptic complexes $[M(L_1)_n(L_2)_m]$ in accordance with the present invention allow to combine large solubilities with high $T_g$ values without detrimental effect on the emission properties: they emit in the same color range and almost as efficiently as the homoleptic complexes $[M(L_1)_{m+n}]$ involving the sole $L_1$ ligand.

Although emitting on the whole in the same color range as the corresponding homoleptic complexes, the heteroleptic complexes $[M(L_1)_n(L_2)_m]$ in accordance with the present invention show rather unexpectedly somewhat red-shifted emission compared to the corresponding homoleptic complexes. This red shift is less pronounced with $L_2$ ligand pertaining to formula 2 than with $L_2$ ligand pertaining to formula 1. The extent of this red-shift could thus be tuned according to the nature of the $L_2$ ligand (from formula 1 or formula 2). When used in light-emitting device in combination with only a blue emitter or with both a blue and a green emitter, the orange/red emitting heteroleptic complexes in accordance with the present invention wherein $L_1$ ligand pertains to formulae 3 or 4 should allow to get more easily CIE (x,y) coordinates close to illuminant A (0.45, 0.41) given their red-shifted emission.

Furthermore, the heteroleptic complexes $[M(L_1)_n(L_2)_m]$ in accordance with the present invention show broader emission peaks than homoleptic complexes $[M(L_1)_{m+n}]$ involving the sole $L_1$ ligand and than more "classical" heteroleptic complexes $[M(L_1)_n(acac)_m]$ and $[M(L_1)_n(pic)_m]$ involving the $L_1$ ligand as "main" ligand and acetylacetonate (=acac) or picolinate (=pic) or their derivatives as "ancillary" ligand. The heteroleptic complexes in accordance with the present invention are therefore particularly well suited for lighting applications. When used in light-emitting device in combination with only a blue emitter or with both a blue and a green emitter, they could indeed lead to the higher CRI values (>80) which are required in high color quality white light sources, because of their broader emission spectra.

Figure 1:
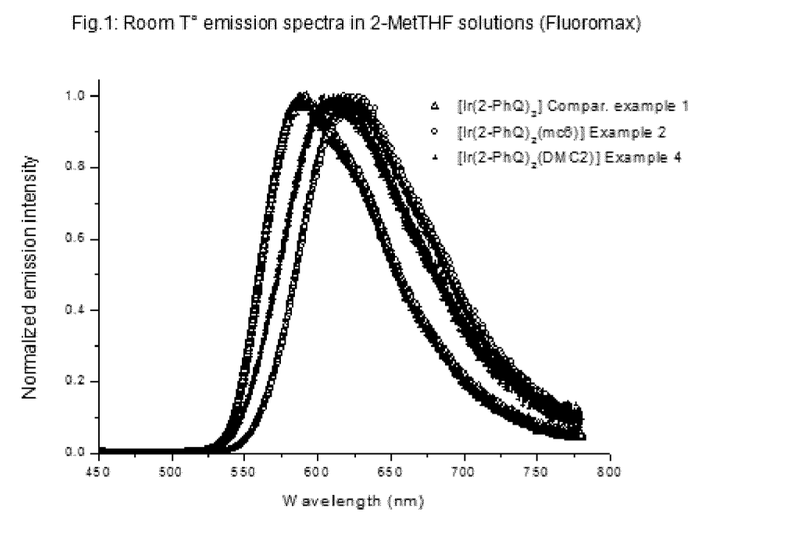
FIG. 1 shows the room temperature emission spectra of the inventive complexes of Examples 2 and 4 compared to that of the complex of Comparative example 1.
Figure 2:
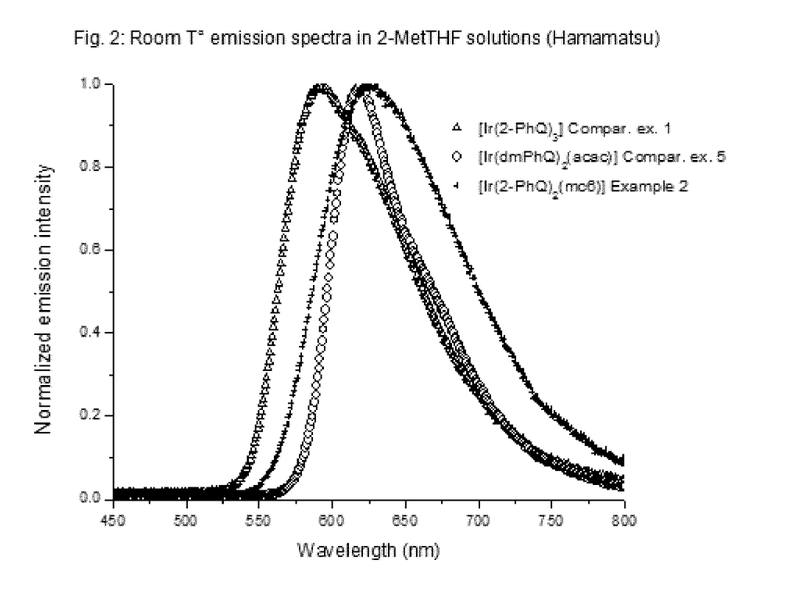
FIG. 2 shows the room temperature emission spectra of the inventive complex of Example 2 compared to those of the complexes of Comparative examples 1 and 5.

FIGS. 1 and 2 show respectively the room temperature emission spectra of the complexes of comparative Example 1 and Examples 2 and 4 and of the complexes of comparative Example 1 and 5 and Example 2 as measured in 2-methyl tetrahydrofurane with the equipment described in the working examples.

Another object of the invention is the use of the light emitting materials as above described in the emitting layer of an organic light emitting device.

In particular, the present invention is directed to the use of the light emitting material as above described as dopant in a host layer, optionally containing other emitter(s), functioning as an emissive layer in an organic light emitting device.

In case of use of the light emitting material (i.e. of the heteroleptic complexes in accordance with the present invention) as dopant in a host layer, it is generally used in an amount of at least 1% wt, preferably of at least 3% wt, more preferably of least 5% wt with respect to the total weight of the host and the dopant and generally of at most 35% wt, preferably at most 25% wt, more preferably at most 15% wt with respect to the total weight of the host and the dopant.

Those light emitting materials in accordance with the present invention, which are orange or red light emitting materials may be combined in the emissive layer with other dopant emitter(s), like blue and green emitters, in order to get white light (WOLED devices). In those cases the light emitting material in accordance with the present invention is generally used in an amount of at least 0.05% wt, preferably of at least 0.1% wt, more preferably of least 0.2% wt with respect to the total weight of the host and dopants and generally of at most 5% wt, preferably at most 3% wt, more preferably at most 1% with respect to the total weight of the host and dopants.

The present invention is also directed to an organic light emitting device (OLED) comprising an emissive layer (EML), said emissive layer comprising the light emitting material or mixture of these materials as above described, optionally with a host material (wherein the light emitting material in accordance with the present invention is preferably present as a dopant), said host material being notably suitable in an EML in an OLED and optionally with other fluorescent or phosphorescent emitters in order to obtain a white light emission.

An OLED generally comprises:
a substrate, for example (but not limited to) glass, plastic, metal;
an anode, generally transparent anode, such as an indium-tin oxide (ITO) anode;
a hole injection layer (HIL) for example (but not limited to) PEDOT/PSS;
a hole transporting layer (HTL);
an emissive layer (EML);
an electron transporting layer (ETL);
an electron injection layer (EIL) such as LiF, $Cs_2CO_3$
a cathode, generally a metallic cathode, such as e.g. an Al layer.

For a hole conducting emissive layer, a hole blocking layer (HBL) may be used that can also act as an exciton blocking layer between the emissive layer and the electron transporting layer. For an electron conducting emissive layer, an electron blocking layer (EBL) may be used that can also act as an exciton blocking layer between the emissive layer and the hole transporting layer. The emissive layer may be equal to the hole transporting layer (in which case the exciton blocking layer is near or at the anode) or to the electron transporting layer (in which case the exciton blocking layer is near or at the cathode).

The emissive layer may be formed with a host material, in which the light emitting material or mixture of these materials as above described resides as a guest, and or the emissive layer may consist essentially of the light emitting material or mixture of these materials as above described itself. In the former case, the host material may be a hole-transporting material e.g. selected from the group of substituted tri-aryl amines. Preferably, the emissive layer is formed with a host material in which the light emitting material resides as a guest. The host material may be an electron-transporting material selected from the group of oxadiazoles, triazoles and ketones (e.g. Spirobifluoreneketones SBFK). Examples of host materials are 4,4'-N,N'-dicarbazole-biphenyl ["CBP"] or 3,3'-N,N'-dicarbazole-biphenyl ["mCBP"] which have the formula:

CBP mCBP

In a preferred embodiment, the host material is a compound represented by the following formulae (9) or (10) or mixtures thereof:

Formula (9)

wherein A is a single bond or a divalent residue of biphenyl, triphenyl, and in each of which one or more hydrogen atoms attached in the carbon atoms may be replaced by a substituent other than hydrogen, wherein Z is any one selected from N, O, S, and $SiR^{16}$, Y is $N—R^{16}$, O, S, $Si(R^{16})_2$ where $R^{16}$ is $C_1$-$C_{20}$ alkyl or $C_1$-$C_{20}$ aryl, $R^{14}$ and $R^{15}$ are independently selected from hydrogen or $C_1$-$C_{20}$ alkyl;

X1 to X4 are independently selected from substituents other than spirobifluorenyl;

l, p and q are integers between 0 to 4;
m is an integer between 0 to 3,

Formula (10)

wherein $B_1$ and $B_2$ are independently selected from hydrogen, and a heterocyclic group;

r is an integer between 0 to 3; and

$X_1$ to $X_4$, m, p, and q are as defined in Formula (9).

Compounds of formulae (9) or (10) are described in WO 2012/048820 to which reference is made herewith for further details.

Preferred compounds of formulae (9) and (10) are compounds I to XIII:

(I)

(II)

(III)

(IV)

(V)

(VI)

(VII)

(VIII)

(IX)

(XII)

(XIII)

(X)

(XI)

Optionally the emissive layer may also contain other emitter(s), fluorescent or phosphorescent, emitting in a wavelength range corresponding to color(s) which is (are) complementary to that of the light emitting materials from the present invention in order to obtain a white light emission.

Optionally, the emissive layer may also contain a polarization molecule, present as a dopant in said host material and having a dipole moment, that generally affects the wavelength of light emitted when said light emitting material as above described, used as dopant, luminesces.

A layer formed of an electron transporting material is advantageously used to transport electrons into the emissive layer comprising the light emitting material and the (optional) host material. The electron transporting material may be an electron-transporting matrix selected from the group of metal quinoxolates (e.g. Alq$_3$, Liq), oxadiazoles triazoles and ketones (e.g. Spirobifluorene ketones SBFK). Examples of electron transporting materials are tris-(8-hydroxyquinoline) aluminum of formula ["Alq$_3$"] and spirobifluoreneketone SBFK:

Alq3

SBFK

A layer formed of a hole transporting material is advantageously used to transport holes into the emissive layer comprising the light emitting material as above described and the (optional) host material. An example of a hole transporting material is 4,4'-bis[N-(1-naphthyl)-N-phenylamino]biphenyl ["α-NPD"].

α-NPD

The use of an exciton blocking layer ("barrier layer") to confine excitons within the luminescent layer ("luminescent zone") is preferred and has proved to be advantageous in many cases. For a hole-transporting host, the blocking layer may be placed between the emissive layer and the electron transport layer. An example of a material for such a barrier layer is 2,9-dimethyl-4,7-diphenyl-1,10-phenanthroline (also called bathocuproine or "BCP"), which has the formula

BCP

BCP.

The above OLEDs comprising phosphorescent emitters in accordance with the present invention can be fabricated by any method conventionally used in the field of organic devices, for example, vacuum evaporation, thermal deposition, printing or coating. The phosphorescent emitters in accordance with the present invention are particularly well suited for solution-processes OLEDs and WOLEDs.

Now, some embodiments will be provided to facilitate the understanding of the present invention. However, it is important to note that the above-described specific embodiments are only described herein for illustrative purposes. The specific procedures, materials or conditions should not be construed in any manner as limiting the scope of the present invention. Further, any other methods, materials or conditions, which are obvious to a person of ordinary skill in the art, are also readily covered by the present invention.

EXAMPLES

Emitters Synthesis

All the reactions were performed in the dark and under inert atmosphere.

All the chloro-bridged dimers [(L)$_2$Ir(μ-Cl)$_2$Ir(L)$_2$] mentioned hereafter in the examples were obtained using a well-known procedure which consists to react IrCl$_3$.xH2O with a slight excess of the ligand compound L-H (2.5 to 3 mol/mol Ir) in a 3:1 (v/v) mixture of 2-ethoxy-ethanol and water at reflux for ≈20 h.

2-PhQ represents the 2-phenylquinoline ligand, M-PhQ represents the 2-phenyl-4-methylquinoline ligand, dmPhQ represents the 2-(3,5-dimethylphenyl)quinoline ligand, n-hexPhQ and tButPhQ represent 2-phenylquinoline ligands having respectively a n-hexyl substituent and a tertiary butyl substituent in the 4 position of the phenyl ring, mc3 represents the 1-(2,6 dimethyl-phenyl)-2-phenyl-1H-imidazole ligand, mc6 represents the 1-(2,6 diisopropyl-phenyl)-2-phenyl-1H-imidazole ligand and DMC2 represents the 5-mesityl-1-phenyl-1H-pyrazole ligand. The homoleptic complex [Ir(2-PhQ)$_3$] was purchased from Rubipy Scientific Inc., [Ir(M-PhQ)$_3$] and [Ir(n-hexPhQ)$_3$] from Lumtec. [Ir(tButPhQ)$_3$] has been prepared in accordance with the preferred process outlined above for the manufacture of the heteroleptic complexes in accordance with the present invention. The heteroleptic complex [Ir(dmPhQ)$_2$(acac)] (with dmPhQ=2-(3,5-dimethylphenyl)quinoline, acac=acetylacetonate) was purchased from Rubipy Scientific Inc.

Example 1

Synthesis of [Ir(2-PhQ)$_2$(mc3)] Heteroleptic Complex

[Ir(2-PhQ)$_2$(mc3)]

To a 100 ml vial flushed with argon were introduced 0.403 g of the chloro-bridged dimer [(2-PhQ)$_2$Ir(μ-Cl)$_2$Ir(2-PhQ)$_2$], 0.239 g of 1-(2,6-dimethylphenyl)-2-phenyl-1H-imidazole mc3 ligand compound (mc3 ligand/dimer molar ratio: 3.0 mol/mol) and 60 ml of a 1:1 v/v mixture of diglyme and water. After sealing, the vial was heated under stirring at 130° C. for 144 hours. After cooling, the precipitate was filtered off with suction and washed with water and hexane. The crude solid was purified by silica gel column chromatography using CH$_2$Cl$_2$/hexane 8:2 (v/v) as the eluent to give 0.263 g of the desired heteroleptic complex (yield: 49%). No other product could be detected by $^1$H-NMR analysis (NMR purity using octamethylcyclotetrasiloxane as internal standard: 100 wt %).

Example 2

Synthesis of [Ir(2-PhQ)$_2$(mc6)] Heteroleptic Complex

[Ir(2-PhQ)$_2$(mc6)]

[Ir(2-PhQ)$_2$(mc6)] heteroleptic complex was obtained using the same conditions as for [Ir(2-PhQ)$_2$(mc3)] in example 1 replacing mc3 ligand compound by mc6 ligand compound. Yield estimated from NMR analysis of the "crude" recovered product was equal to 47%. Isolated yield after purification by silica gel column chromatography using CH$_2$Cl$_2$/hexane 8:2 (v/v) as the eluent was equal to 44%. No other product could be detected by $^1$H-NMR analysis (NMR purity using octamethylcyclotetrasiloxane as internal standard: 100 wt %).

A higher yield (→72% from NMR analysis of the "crude" recovered product) was obtained by using a larger excess of mc6 ligand (mc6 ligand/dimer molar ratio: 7.0 mol/mol), the other conditions being unchanged.

The material was further purified by sublimation.

Example 3

Synthesis of [Ir(tButPhQ)$_2$(mc3)] Heteroleptic Complex

[Ir(tButPhQ)$_2$(mc3)]

[Ir(tButPhQ)$_2$(mc3)] heteroleptic complex was obtained using the same conditions as for [Ir(2-PhQ)$_2$(mc3)] in example 1 replacing the starting dichloro-bridged dimer by the one involving tButPhQ ligand and using a Büchi Miniclave glass autoclave as reactor instead of a sealed vial. Isolated yield after purification by silica gel column chromatography using CH$_2$Cl$_2$/hexane 8:2 (v/v) as the eluent was equal to 45%. No other product could be detected by $^1$H-NMR analysis (NMR purity using octamethylcyclotetrasiloxane as internal standard: 98 wt %).

The material was further purified by sublimation.

Example 4

Synthesis of [Ir(2-PhQ)$_2$(DMC2)] heteroleptic complex

[Ir(2-PhQ)$_2$(DMC2)]

[Ir(2-PhQ)$_2$(DMC2)] heteroleptic complex was obtained using the same conditions as for [Ir(2-PhQ)$_2$(mc3)] in example 1 replacing mc3 ligand compound by DMC2 ligand compound. Isolated yield after purification by silica gel column chromatography using CH$_2$Cl$_2$/hexane 8:2 (v/v) as the eluent was equal to 35%. No other product could be detected by $^1$H-NMR analysis (NMR purity using octamethylcyclotetrasiloxane as internal standard: 100 wt %). The material was further purified by sublimation.

Emitters Characterization

Solubility evaluation were performed at 25° C. using toluene as solvent.

The photoluminescence measurements have been performed on highly diluted (≈10$^{-5}$ mol/l) emitters solutions in spectroscopic grade 2-methyl-THF using a HORIBA JOBIN WON Fluoromax −4 P spectrofluorimeter. Measurements at 77 K were carried out using the FL-2013 Dewar liquid nitrogen assembly from HORIBA JOBIN YVON. The measured wavelengths corresponding to the emission peak(s) maxima (λmax) are reported in table 1.

The photoluminescence quantum yield (Φ) measurements have been performed using a HAMAMATSU C11347-11 Quantaurus-QY absolute photoluminescence quantum yield spectrometer. The measurements have been carried out at room temperature on diluted (≈10$^{-5}$ mol/l) emitters solutions in spectroscopic grade 2-methyl-THF which have been degassed in the quartz cuvette used for the measurements by bubbling with argon for 15 min before measurement. The full width at half maximum (FWHM) of the emission peak observed at room temperature reported in table 1 are those estimated from the emission spectra obtained using the HAMAMATSU absolute photoluminescence quantum yield spectrometer.

The glass transition temperatures T$_g$ were measured using a TA instruments 2920 DSC equipment and data evaluation were done with the TA Instruments Universal Analysis 2000 software.

All these results are collected in Table 1.

TABLE 1

|  | Toluene solubility S at 25° C. (wt %) | Emission properties | | | | |
|---|---|---|---|---|---|---|
|  |  | $\lambda_{max}$ room T (nm) | $\lambda_{max}$ 77 K (nm) | FWHM (nm) | Φ (%) | $T_g$ (° C.) |
| [Ir(2-PhQ)$_2$(mc3)] Example 1 | 0.22 < S < 0.24 | 624 | 577/621 | 115 | 62 | — |
| [Ir(2-PhQ)$_2$(mc6)] Example 2 | 0.38 < S < 0.46 | 624 | 578/620 | 115 | 56 | — |
| [Ir(tButPhQ)$_2$(mc3)] Example 3 | S > 3.8 | 626 | — | 117 | 51 | 176 |
| [Ir(2-PhQ)$_2$(DMC2)] Example 4 | S > 0.25 | 611 | 562/603 | 116 | 62 | — |
| [Ir(2-PhQ)$_3$] Comp. example 1 | S < 0.02 | 589 | 561/605 | 100 | 61 | — |
| [Ir(M-PhQ)$_3$] Comp. example 2 | 0.08 < S < 0.09 | 584 | — | 97 | 80 | — |
| [Ir(n-hexPhQ)$_3$] Comp. example 3 | S > 1.0 | 596 | — | — | — | 54 |
| [Ir(tButPhQ)$_3$] Comp. example 4 | 0.22 < S < 0.30 | 593 | 568/612 | — | — | — |
| Ir(dmPhQ)$_2$(acac) Comp. example 5 | 0.07 < S < 0.37 | 616 | — | 72 | 72 | — |

In Table 1 $\lambda_{max}$ room T and $\lambda_{max}$ 77 K represent the emission maxima at room temperature and 77 K, respectively, FWHM represents the full width at half maximum of the emission peak, i.e. the width of the wavelength range of the emission peak between the two points for which the emission is at least half of the maximum emission. Φ represents the photoluminescence quantum yield measured in 2-methyl tetrahydrofurane solution.

From the comparison of comparative example 1 with examples 1, 2 and 4 as well as the comparison of comparative example 4 with example 3, it appears clearly that the solubility of the heteroleptic complexes in accordance with the present invention exceeds the solubility of the respective homoleptic complex by a factor of at least 10. This is a highly important advantage in the course of the manufacture of organic electronic devices by solution processing and thus constitutes a significant economic and technical advantage.

The introduction of a n-hexyl substituent on the phenyl ring of the phenylquinoline (comparative example 3) allows also for a large increase of the Ir(n-hexPhQ)$_3$ emitter solubility as compared to Ir(2-PhQ)$_3$ (from <0.02 wt % to >1 wt %) but this is at the expense of the glass transition temperature $T_g$ which concomitantly becomes very low ($T_g$=54° C.) leading to problems during operation of the OLED devices. On the contrary, the heteroleptic complexes in accordance with the present invention allow to combine a large solubility with a high $T_g$ value, as shown by example 3 (S>3.8 wt % and $T_g$=176° C.).

The heteroleptic complexes in accordance with the present invention which combine L$_1$ phenylquinoline type ligand(s) with L$_2$ phenylimidazole (formula 1) or phenylpyrazole (formula 2) type ligand(s) prove as efficient emitters as corresponding homoleptic complexes based on the sole phenylquinoline type ligand: Φ values of examples 1, 2 and 4 (respectively 62, 56 and 62) in table 1 appear as high as that of comparative example 1 (=61).

The emission of the heteroleptic complexes in accordance with the present invention occurs on the whole in the same orange-red color range as the corresponding homoleptic complexes but is rather unexpectedly somewhat red-shifted as compared to the corresponding homoleptic complexes as shown by FIG. 1 and by the comparison in table 1 of $\lambda_{max}$ values of examples 1, 2 and 4 with comparative example 1 as well as the comparison of $\lambda_{max}$ value of example 3 with comparative example 4. This red shift is less pronounced with phenylpyrazole type ligand (formula 2) as L$_2$ ligand, as shown by comparison of $\lambda_{max}$ values of examples 1 and 2 (phenylimidazole as L$_2$ ligand) with example 4 (phenylpyrazole as L$_2$ ligand). The extent of this red-shift could thus be tuned according to the nature of the L$_2$ ligand, phenylimidazole or phenylpyrazole type. When used in light-emitting device in combination with only a blue emitter or with both a blue and a green emitter, the heteroleptic complexes in accordance with the present invention should allow to get more easily CIE (x,y) coordinates close to illuminant A (0.45, 0.41) given their red-shifted emission.

As shown by FIG. 2 and the values of the full width at half maximum (FWHM) of emission peaks reported in table 1, the heteroleptic complexes in accordance with the present invention which combine L$_1$ phenylquinoline type ligand(s) with L$_2$ phenylimidazole or phenylpyrazole type ligand(s) show broader emission peaks (examples 1 to 4: 115-117 nm) than homoleptic complexes involving only phenylquinoline type ligand (comparative examples 1 and 2: 97-100 nm) and heteroleptic complexes involving phenylquinoline type ligand as main ligand and acetylacetonate (acac) as ancillary ligand (comparative example 5: 72 nm). The heteroleptic complexes in accordance with the present invention are therefore particularly well suited for lighting applications. When used in light-emitting devices in combination with only a blue emitter or with both a blue and a green emitter, they will indeed allow to reach the higher CRI values (>80) which are beneficial in lighting applications, given their broader emission spectra.

This has been demonstrated by comparing the photoluminescence quantum yield (Φ) and color rendering index (CRI) of two emissive layers (EMLs) having exactly the same composition but differing only by the type of red emitter used, either [Ir(tButPhQ)$_2$(mc3)] according to our invention (example 3) or the commercial red emitter [Ir(dmPhQ)$_2$(acac)] (comparative example 5). The photoluminescence quantum yield Φ was measured in a HAMAMATSU C11347-11 Quantaurus-QY, using 60 nm-thick films of the EMLs spincoated onto fused silica substrates. The CRIs were derived from the steady-state photoluminescence (PL) spectra of the same samples, also measured in the Quantaurus-QY system. The EMLs consisted of a red and a blue emitter dispersed into a high triplet energy host, such as one of those described in WO 2012/048820 referred to hereinabove. The ratios of the two emitters in the host matrix were chosen so that the x- and y-CIE coordinates of the two types of emissive layers were both within 0.05 of the CIE coordinates of Illuminant A (0.45, 0.41). The Φ values of both types of EMLs were close, at 72 and 73% respectively for the EML containing [Ir(dmPhQ)$_2$(acac)] and [Ir(tButPhQ)$_2$(mc3)]. However, the two EMLs differed quite drastically by their CRI, which was found to be 64 for the EML containing [Ir(dmPhQ)$_2$(acac)] and 83 for the EML made using [Ir(tButPhQ)$_2$(mc3)]. A CRI>80 is beneficial for high color quality white light sources, therefore indicating that the heteroleptic complexes in accordance with the present invention are particularly well suited for the design of phosphorescent WOLEDs for lighting applications The heteroleptic complexes in accordance with the present invention are particularly well suited for producing white light emission when used in an organic light-emitting device in combination with only a blue emitter or with both a blue and a green emitter. They are thus particularly well suited to solution-processed WOLEDs (=white organic light-emitting diodes).

The invention claimed is:

1. A heteroleptic light emitting complex having the general formula $M(L_1)_m(L_2)_n$ wherein
    a) $L_1$ is selected from substituted or unsubstituted 2-phenylquinoline and substituted or unsubstituted 1-phenylisoquinoline ligands of formulae (3) and (4)

wherein $R^8$ to $R^{13}$, which may be the same or different at each occurrence, are selected from the group consisting of H, halogen, NO$_2$, CN, N(R$^6$)$_2$, B(OR$^6$)$_2$, COOH, C(O)R$^6$, CO$_2$R$^6$, CON(R$^6$)$_2$, OR$^6$, SR$^6$, SO$_3$H, S(=O) R$^6$, S(=O)$_2$R$^6$, P(R$^6$)$_2$, P(=O)(R$^6$)$_2$, Si(R$^6$)$_3$, alkyl, alkenyl, alkynyl, aryl, substituted aryl, alkylaryl, heteroaryl, substituted heteroaryl and heterocyclic groups, with R$^6$, which may be the same or different, being selected from the group consisting of H, alkyl, alkenyl, alkynyl, aryl, substituted aryl, alkylaryl, halogen, heteroaryl, substituted heteroaryl and heterocyclic groups, p, u and v, independent of one another, represent an integer of from 0 to 4, t represents an integer from 0 to 3 and s and w, independent of one another represent an integer of from 0 to 2, b) ligand L$_2$ is selected from the group consisting of 1-(2,6 disubstituted phenyl)-2-phenyl-1H-imidazole ligands or 5-(2,6 disubstituted phenyl)-1-phenyl-1H-pyrazole ligands of formulae 1 or 2 wherein
R$^1$ and R$^2$, which may be the same or different, each represent a C$_1$ to C$_{20}$ alkyl or haloalkyl group, a cycloalkyl group, a C$_5$ to C$_{30}$ aryl group or a C$_2$ to C$_{30}$ heteroaryl group, said cycloalkyl, aryl and heteroaryl groups being un-substituted or substituted by substituents selected from the group consisting of halogen, alkyl, alkoxy, amino, cyano, alkenyl, alkynyl, arylalkyl, aryl and heteroaryl groups; and R$^3$ is selected from the group consisting of H, halogen, NO$_2$, CN, N(R$^4$)$_2$, B(OR$^4$)$_2$, COOH, C(O)R$^4$, CO$_2$R$^4$, CON(R$^4$)$_2$, OR$^4$, SR$^4$, SO$_3$H, S(=O)R$^4$, S(=O)$_2$R$^4$, P(R$^4$)$_2$, P(=O)(R$^4$)$_2$, Si(R$^4$)$_3$, alkyl, cycloalkyl, haloalkyl, alkoxy,alkenyl, alkynyl, aryl, alkylaryl, heteroaryl, substituted heteroaryl and heterocyclic groups, with the proviso that R$^3$ is not aryl if ligand L$_2$ is represented by formula 1, R$^4$ which may be the same or different, are selected from the group consisting of H, alkyl, alkenyl, alkynyl, aryl, substituted aryl, alkylaryl, halogen, heteroaryl, substituted heteroaryl and heterocyclic groups, R and R', independently of one another, are selected from the group consisting of H, halogen, NO$_2$, CN, N(R$^5$)$_2$, B(OR$^5$)$_2$, COOH, C(O)R$^5$, CO$_2$R$^5$, CON(R$^5$)$_2$, OR$^5$, SR$^5$, SO$_3$H, S(=O)R$^5$, S(=O)$_2$R$^5$, P(R$^5$)$_2$, P(=O) (R$^5$)$_2$, Si(R$^5$)$_3$, alkyl, alkenyl, alkynyl, aryl, substituted aryl, alkylaryl, heteroaryl, substituted heteroaryl and heterocyclic groups, R$^5$ which may be the same or different, are selected from the group consisting of H, alkyl, alkenyl, alkynyl, aryl, substituted aryl, alkylaryl, halogen, heteroaryl, substituted heteroaryl and heterocyclic groups, a is an integer of from 0 to 3 and b is an integer of from 0 to 2, and c is an integer of from 0 to 3, c) M is Ir, m is 2, and n is 1.

2. The heteroleptic light emitting complex in accordance with claim 1, wherein ligand L$_2$ is selected from 1-(2,6 disubstituted phenyl)-2-phenyl-1H-imidazole ligands of formula (1) wherein $R^3$ is H or a $C_1$ to $C_{20}$ alkyl group.

3. The heteroleptic light emitting complex in accordance with claim 1 wherein ligand $L_2$ is selected from 5-(2,6 disubstituted phenyl)-1-phenyl-1H-pyrazole ligands of formula (2) wherein $R^3$ is H or a $C_1$ to $C_{20}$ alkyl group.

4. The heteroleptic light emitting complex in accordance with claim 1 wherein at least one of $R^1$ and $R^2$ is a $C_1$ to $C_{20}$ alkyl group.

5. The heteroleptic light emitting complex in accordance with claim 4 wherein $R^1$ and $R^2$ are independently selected from $C_1$ to $C_8$ alkyl groups.

6. The heteroleptic light emitting complex in accordance with claim 5 wherein $R^1$ and $R^2$ are independently selected from methyl and isopropyl.

7. The heteroleptic light emitting complex in accordance with claim 1 represented by any one of formulae (5) to (8):

(5)

(6)

(7)

(8)

wherein $R^1$ to $R^3$ have the meanings as defined in claim 1 and wherein the phenylquinoline and phenylisoquinoline ligands may be substituted or unsubstituted.

8. The heteroleptic light emitting complex in accordance with claim 1 wherein ligand $L_1$ is a 2-phenylquinoline ligand and ligand $L_2$ is a ligand of formula (2).

9. The heteroleptic light emitting complex in accordance with claim 1 wherein the triplet energy level of ligand $L_2$ is higher than the triplet energy level of ligand $L_1$.

10. An emitting layer of an organic light emitting device comprising the heteroleptic light emitting complex according to claim 1.

11. An organic light emitting device comprising an emissive layer, said emissive layer comprising a heteroleptic light emitting complex according to claim 1.

12. An organic light emitting device comprising an emissive layer, said emissive layer comprising a heteroleptic light emitting complex according to claim 1 as dopant and a host material represented by general formulae (9) or (10) :

Formula (9)

wherein A is a single bond or a divalent residue of biphenyl, triphenyl, and in each of which one or more hydrogen atoms attached in the carbon atoms may be replaced by a substituent other than hydrogen, wherein Z is any one selected from N, O, S, and $SiR^{16}$, Y is N—$R^{16}$, O, S, $Si(R^{16})_2$ where $R^{16}$ is $C_1$-$C_{20}$ alkyl or $C_1$-$C_{20}$ aryl, $R^{14}$ and $R^{15}$ are independently selected from hydrogen or $C_1$-$C_{20}$ alkyl;

$X_1$ to $X_4$ are independently selected from substituents other than spirobifluorenyl;

l, p and q are integers between 0 to 4;

m is an integer between 0 to 3,

Formula (10)

wherein $B_1$ and $B_2$ are independently selected from hydrogen, and a heterocyclic group;
r is an integer between 0 to 3; and $X_1$ to $X_4$, m, p, and q are as defined for Formula (9).

* * * * *